(12) United States Patent
Lemmens et al.

(10) Patent No.: US 6,521,758 B2
(45) Date of Patent: Feb. 18, 2003

(54) TOSYLATE SALTS OF 4-(P-FLUOROPHENYL)-PIPERIDINE-3-CARBINOLS

(75) Inventors: Jacobus M. Lemmens, Mook (NL); Theodorus H. A. Peters, Arnhem (NL); Pavel Slanina, Lelekovice (CZ)

(73) Assignee: Synthon BV (NL)

( * ) Notice: Subject to any disclaimer, the term of this patent is extended or adjusted under 35 U.S.C. 154(b) by 0 days.

(21) Appl. No.: 09/853,898

(22) Filed: May 14, 2001

(65) Prior Publication Data

US 2002/0082277 A1 Jun. 27, 2002

(30) Foreign Application Priority Data

May 12, 2000 (NL) .................. PCT/NL00/00320

(51) Int. Cl.[7] ...................... C07D 211/06; C07D 211/20
(52) U.S. Cl. ................... 546/197; 546/198; 546/205; 546/206; 546/236
(58) Field of Search ............... 546/197, 198, 546/205, 206, 236

(56) References Cited

U.S. PATENT DOCUMENTS

| 3,912,743 A | | 10/1975 | Christensen et al. ........ 546/197 |
|---|---|---|---|
| 4,007,196 A | | 2/1977 | Christensen et al. ........ 546/197 |
| 4,585,777 A | | 4/1986 | Lassen et al. ............... 514/317 |
| 4,902,801 A | | 2/1990 | Faruk et al. ................ 546/220 |
| 5,874,447 A | * | 2/1999 | Benneker et al. ........... 546/197 |

FOREIGN PATENT DOCUMENTS

| EP | 0190496 | * | 8/1986 | ................. 546/197 |
|---|---|---|---|---|
| EP | 0 300 617 A1 | | 1/1989 | ................. 546/197 |
| EP | 0 802 185 A1 | | 10/1997 | ................. 546/197 |
| EP | 0 810 225 A1 | | 12/1997 | ................. 546/197 |
| EP | 0812827 | * | 12/1997 | ................. 546/197 |
| EP | 0 812 827 A1 | | 12/1997 | ................. 546/197 |
| WO | 93/22284 | | 11/1993 | ................. 546/197 |
| WO | 94/03428 | | 2/1994 | ................. 546/197 |
| WO | 96/36636 | | 11/1996 | ................. 546/197 |
| WO | 98/01424 | | 1/1998 | ................. 546/197 |
| WO | WO 98/01424 | * | 1/1998 | ................. 546/197 |
| WO | WO 01/85689 | * | 11/2001 | ................. 546/197 |

* cited by examiner

Primary Examiner—Alan L. Rotman
Assistant Examiner—Raymond Covington
(74) Attorney, Agent, or Firm—Fleshner & Kim, LLP

(57) ABSTRACT

Tosylate salts are useful in purifying 4-(fluorophenyl)-3-carbinol-piperidines from the corresponding des-fluoro impurity. The purified compounds are advantageously used in paroxetine synthesis.

25 Claims, No Drawings

TOSYLATE SALTS OF 4-(P-FLUOROPHENYL)-PIPERIDINE-3-CARBINOLS

The present application claims the benefit of priority under 35 U.S.C. § 119 from PCT/NL00/00320, filed May 12, 2000, the entire contents of which are incorporated herein by reference.

BACKGROUND OF THE INVENTION

The present invention relates to a tosylate salt of 4-fluorophenyl-3-carbinol piperidine compounds and to the use thereof in purifying 4-fluorophenyl-3-carbinol piperidine compounds against des-fluoro impurities. 4-(p-fluorophenyl)-piperidine 3-carbinols of the general formula (1)

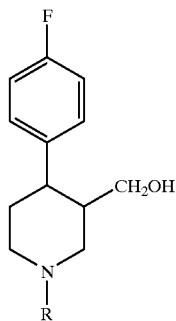

(1)

wherein R represents a hydrogen, alkyl, aryl or aralkyl group, are key intermediates in the synthesis of the pharmaceutically active compound paroxetine, represented by the formula (2).

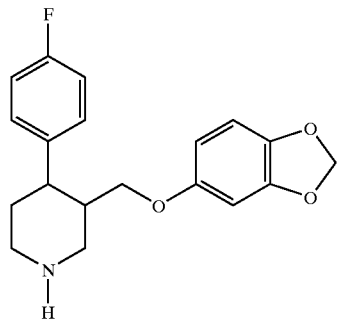

(2)

Several industrially applicable synthetic procedures leading to compounds of the formula (1) have been described in the prior art.

U.S. Pat. No. 3,912,743 describes the reduction of 4-aryl-3-piperidinecarboxylic acid esters of the general formula (3) with lithium aluminium hydride,

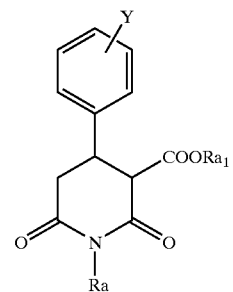

(3)

wherein Ra is an alkyl or aryl group, Ra1 is a lower alkyl group, Y is hydrogen, a halogen atom, a methoxy group or a mercapto group.

EP 223334, corresponding to U.S. Pat. No. 4,902,801, describes reduction of 4-aryl-2,6-dioxo-3-piperidinecarboxylic acid esters of the general formula (4) with lithium aluminium hydride,

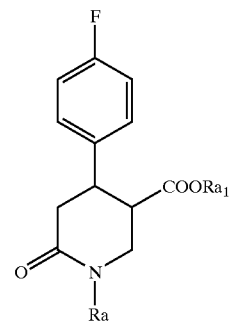

(4)

wherein Ra is hydrogen, a lower alkyl group or an aralkylgroup, Ra1 is a lower alkyl group, Y is hydrogen, a halogen atom, a lower alkyl group, an aralkylgroup or a trifluoroalkyl group.

EP application 802185 describes the reduction of trans-4-aryl-6-oxopiperidine-3-carbinols of the general formula (5) by hydrides or metal hydrides, (5)

wherein Y is hydrogen, halogen, alkyl group, aryl group, an aralkyl group etc., Ra is hydrogen, lower alkyl group or an aralkyl group, Ra1 is hydrogen, a lower alkyl group, an aryl group or an aralkyl group.

PCT application WO 96/36636 discloses a reduction of the tetrahydropyridine carbinols of the formula (6)

(6)

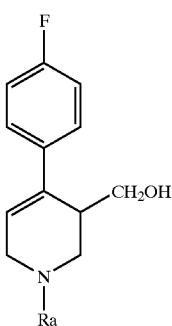

wherein Ra is C2–C5-alkyl, phenyl-C1–C5-alkyl or substituted phenyl-C1–C5-alkyl group, by a metal hydride There are two centres of optical chirality in the molecule of 4-arylpiperidine-3-carbinols of the above formula (1), and there may exist four optical isomers thereof. As the final pharmaceutically active product paroxetine is a single (−)trans (3S,4R) isomer, it is highly desired that the piperidine-3-carbinols of the formula (1) are produced from a, preferably (3S,4R)trans, stereoisomer with high optical purity.

Accordingly, the starting compounds preferably have trans-configuration on carbons 3 and 4, whereby an additional step of optical resolution is preferably included in all the above-described synthetic processes of the prior art, before or after the reduction. Such resolution processes are known from the prior art.

In the known reduction procedures, an excess of hydride reducing agent is required for a successful and complete reduction of the precursor. The hydride agent however also causes an undesired hydrogenolysis side- reaction resulting in defluorination of the phenyl ring, even under mild reaction conditions, whereby a certain amount of a desfluorinated impurity of the formula (7), (7)

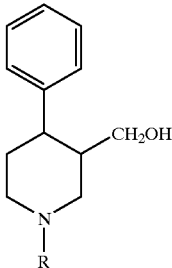

wherein R has the same meaning as in formula (1), is formed. This side product is more problematically formed when carrying out the processes on an industrial scale, as a result of overloading with the hydride and overheating, since charging with the reducing agent and temperature control is not as efficient as in the laboratory.

The impurity (7) is consequently the source of the most common impurity in the final paroxetine, namely the de-fluorinated, or des-fluoro, paroxetine, as the des-fluoro impurity (7) undergoes the same chemical transformations in the process of paroxetine production. If paroxetine is used as a pharmaceutical substance, the content of the des-fluoro paroxetine therein should be less than 0.1% according to Pharmacopoeia prescriptions (e.g. Paroxetine hydrochloride USP XXIII).

The purification of (1) and subsequent compounds from the corresponding des-fluoro impurities is difficult. The known procedures of optical resolution of racemic (1) into enantiomers by fractional crystallization of salts with optically active acids are not efficient if aimed to remove the des-fluoro impurity. In fact, the amount of undesired desfluoro-impurity in the racemic and resolved product is not substantially decreased by such resolution. The content of the structurally related des-fluoro impurities is also not substantially decreased within the next synthetic steps leading to paroxetine.

Usually, the content of des-fluoro impurity in raw (1) is approx. 0.5–1.5% (w/w) and may be even higher, namely in the industrial scale as explained above. It is apparent that if a reduction method produces compound (1) contaminated with an undesired amount of des-fluoro impurity, some further purification is necessary. Such purification should preferably be made in as early a stage as possible since purification in later synthetic steps is economically less favourable. However, conventional crystallizations are either ineffective or provide low yields, causing losses of the product and making the overall production procedure lengthy and economically undesirable. Thus, it is highly desired to find a process for separating raw 4-arylpiperidine-3-carbinols of the general formula (1) from its corresponding des-fluoro impurity (7) which would allow the industrial producer to minimise the amount of the des-fluoro impurity in (1) to such level that, subsequently, the produced paroxetine will contain less than about 0.1% of the des-fluoro paroxetine.

SUMMARY OF THE INVENTION

The present invention relates to the discovery that 4-arylpiperidine-3-carbinols as defined by the general formula (1) (frequently referred hereinafter as to "compounds (1)"), particularly the trans-racemates thereof, and more particularly the (3S,4R)-trans single optical isomers thereof, can be efficiently purified in respect of the content of the des-fluoro impurity (7), by conversion of the raw compound (1) into a salt thereof with toluene sulfonic acid, preferably p-toluene sulfonic acid and crystallisation of the resulted p-toluene sulfonate salt from a solution in an appropriate solvent.

A first aspect of the present invention relates to a salt compound of the formula (8):

(8)

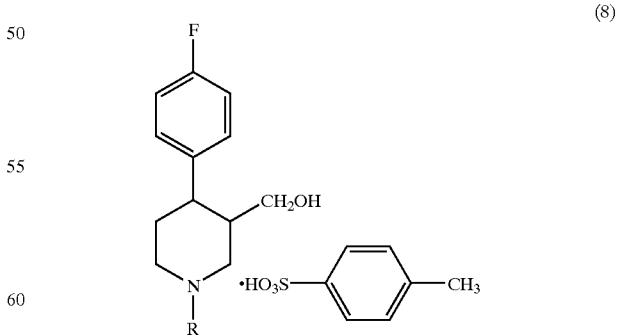

Wherein R is hereinafter defined.

A second aspect of the present invention relates to a process which comprises contacting a compound of formula (1)

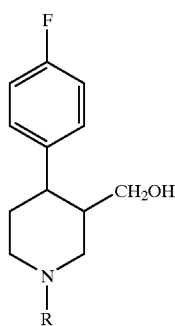

(1)

or a salt thereof which contains a des-fluoro impurity of formula (7)

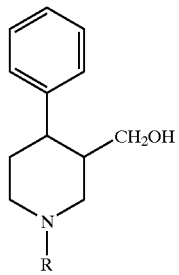

(7)

wherein R in both compounds (1) and (7) represents a hydrogen atom, a lower alkyl group, an aryl group, an aralkyl group, an alkoxycarbonyl group or an aryloxycarbonyl group, with toluene sulfonic acid in a solvent to form a salt of formula (8).

DETAILED DESCRIPTION OF THE INVENTION

The present invention provides a simple, industrially applicable and high-yield purification process which enables a reduction in the amount of des-fluoro impurity in the produced raw compound (1) both in a form of a racemate or as a single enantiomer, so that pharmaceutically acceptable paroxetine can be produced from (1) without a need of specific purification techniques applied in later steps.

By wording "raw compound (1)", it should be understood a compound (1) as defined above whenever it contains more than 0.2% of the des-fluoro impurity.

Accordingly, an aspect of the invention relates to a process of purification of raw compounds of formula (1) wherein R represents a hydrogen atom, a lower alkyl group, an aryl group, or an aralkyl group, comprising the step of:
  contacting a raw compound of formula (1) or salt thereof with toluene sulfonic acid, preferably p-toluene sulfonic acid, under reactive conditions, most preferably in the presence of a solvent.

A further preferred step includes:
  isolating the formed p-toluene sulfonate salt of compound of the formula (1), preferably in a solid state by means of crystallisation or precipitation from the solution and, optionally, any of the following steps:
    recrystallization of the p-toluene sulfonate salt and/or converting the isolated salt back to the compound of formula (1),
whereby the amount of a desfluoro-impurity present in the raw compound of formula (1) is reduced to a level below about 0.2%.

Particularly, the above process is provided for purification of (−)trans-4-(p-fluorophenyl)-1-methyl-3-piperidinecarbinol (formula (1), R=methyl), also known as paroxol, or more specifically (−)N-methylparoxol from the corresponding des-fluoro impurity, preferably for use in the synthesis of paroxetine.

Another aspect of the present invention relates to a p-toluene sulfonate (tosylate) salt of a compound of formula (1), i.e. to the compound of formula (8):

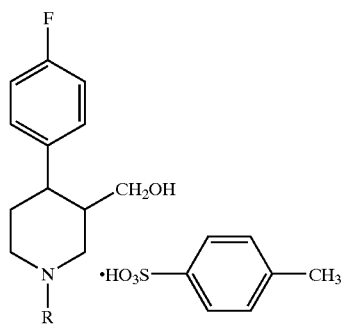

(8)

wherein R has the same meaning as defined for compounds (1).

Particularly, it is understood that the compound of Formula (8) in solid state embraces also the hydrate and solvate form thereof. Furthermore, the formula (8) itself embraces any cis and trans forms, both individually and in mixtures, as well as the individual or racemic mixtures of the optical isomers of each cis and trans forms.

A preferred compound of the present invention is (−)trans-4-(p-fluorophenyl)-1-methyl-3-piperidinecarbinol p-toluene sulfonate (formula (8), R=methyl), particularly a monohydrate thereof.

Preferably the compound of the formula (8) is substantially free of the corresponding des-fluoro impurity. In this context, the wording "substantially free" means that the content of the corresponding des-fluoro impurity is less than about 0.2%. It is a feature of the so defined compound that, if employed as an intermediate in the production of paroxetine of pharmaceutical quality, no subsequent purification step for minimalization of the des-fluoro impurity content is required.

For purposes of this application, the term "lower alkyl" means a straight or branched saturated alkyl group of 1 to 6 carbon atoms or a vinyl group.

Particularly preferred are methyl or ethyl groups and more particularly the methyl group.

An "aryl" group means phenyl group or a phenyl group substituted by one or more halogen, lower alkyl or alkyloxy groups.

An "aralkyl "group means a C1–C4 alkyl group bearing an arylgroup as defined previously, particularly it means a benzyl group.

The terms trans- or cis- configuration mean that the phenyl substituent in position 4 and the carbinol or carboxy substituent in position 3 are in trans- or cis- configuration to each other. The piperidine carbinols represented by the general formula (1) are preferably in trans configuration, due to their preferred application in making paroxetine. The scope of the invention is not however limited to those trans-compounds.

Because there are two asymmetric centres in the molecule, the carbinol of the formula (1) can exist in four enantiomers. It is preferred but not required, due to intended use, that the carbinol of the formula (1) is a single (3S,4R) trans enantiomer. For most of the compounds of formula (1) the (3S,4R) trans enantiomer is a (−) rotating optical isomer. However it is possible that certain combinations of substituents could reverse the direction of optical rotation. For clarity, the R,S nomenclature is frequently used throughout the specification while the (+−) nomenclature is used where appropriate and should not be taken as being contradictory thereto.

The process of the present invention starts with a raw compound (1) whenever produced by means of reduction of a precursor but is not limited thereto. Convenient production methods are exemplified in the introduction. As the reductant, a hydride reductant such as metal hydride reductant, or a borane reductant are generally employed. Suitable examples include lithium aluminium hydride, sodium borohydride, sodium bis(2-methoxyethoxy) aluminium hydride, aluminium hydride, diborane, borane complexes such as borane/tetrahydrofuran and the like.

The process of preparing a solution of the tosylate salt of the present invention is performed simply by contacting the raw compound (1) with a toluene sulfonic acid preferably p-toluene sulfonic acid or its salt optionally in an appropriate solvent system. Any of these two reagents may be charged or brought into a reaction vessel in solid state or in solution.

The choice of the solvent system is optional to such solvent or a mixture of solvents in which the produced sulfonate salt (8) is poorly soluble, as the salt should precipitate out from the solution in solid state, while the same salt of the des-fluoro impurity (7) remains dissolved in the liquid. A convenient solvent is ethyl acetate, water or a 1:1 mixture of methanol and ethyl acetate.

P-toluene sulfonic acid may be added to raw compound (1) in an approximately equimolar amount, below equimolar amount or in slight molar excess; the optimum is such an amount where the efficiency of the process and the yield are properly balanced.

Preferably, the p-toluenesulfonic acid is added in about 0.8–1.5 molar amount, calculated to the raw (1), most preferably in about 1.2 molar amount.

Alternatively, the compound (1) may be brought into contact with p-toluene sulfonic acid in a form of a salt with an acid that is weaker than p-toluene sulfonic acid. Such salt may be a salt with an acid which is commonly used in resolution of racemic (1) to the enantiomers thereof, e.g. O,O-di-p-toluoyltartaric acid, O,O-dibenzoyltartaric acid, (+)-2-nitrotartranilic acid, (+)-2-chlorotartranilic acid etc.

The tosylate salt precipitation can be provided by conventional methods such as crystallisation after cooling the salt solution; direct precipitation after mixing the components; precipitation by using a contrasolvent; crystallisation after concentration of the solution; or by combination of these techniques. A seeding crystal may be used for initiating the precipitation process.

Precipitated salt is isolated from the reaction mixture by filtration or centrifugation; washing the solid with appropriate washing liquid and drying the solid is also recommended. Dependent on the solvent system, isolation technique, washing and drying conditions, the salt may be isolated as a hydrate or as a solvate.

The tosylate salt can be converted back to compound (1) by conventional neutralisation with an equimolar amount of a strong base, preferably an inorganic base such as sodium or potassium hydroxide, in an aqueous medium for example, followed by separation from the inorganic salts, e.g. by extraction into a water immiscible solvent and isolation of the compound (1) from the solution as a free base or as an acid addition salt.

If required, for example when the starting raw (1) contains considerably large amounts of the impurity (7), the whole process or only the precipitation step of the tosylate salt may be repeated. In this step, the reprecipitation (recrystallization) of the tosylate salt can be performed by adding fresh p-toluene sulfonic acid in 0.1–0.5 molar amount.

Among the compounds represented by the general formula (8), are those preferred in which R is a hydrogen, methyl or benzyl group.

Particularly preferred is a compound where R is a methyl group and the formula (8) represents the (3S,4R)trans isomer of said compound.

The salts may be identified and/or characterised by one or more of the following procedures: high performance liquid chromatography, elemental analysis, nuclear magnetic resonance spectroscopy and infrared spectroscopy. The amount of the des-fluoro impurity (7) in products (1) and (8) can be monitored by HPLC, preferably using a reference substance (7) prepared according to the known methods.

This process is particularly suitable for purification of trans (−)-N-methyl-4-p-fluorophenyl-piperidine-3-carbinol (compound (1), R=methyl; hereinunder: (−)N-methyl paroxol) which is a most preferred compound useful in the synthesis of paroxetine.

In a preferred embodiment, the raw starting (−)N-methyl paroxol is suspended in water at elevated temperature (at least 40 C.) and p-toluene sulfonic acid monohydrate is added as a solid in 1.1–1.4 molar amount. The clear solution may be optionally filtered to remove other impurities and the p-toluene sulfonate salt of (−)N-methylparoxol precipitates after cooling. The precipitate is separated by filtration and optionally dried. It is advantageous that dry or wet tosylate salt is analysed for the content of the desfluoro-impurity by a suitable analytical method such as HPLC. Under the described conditions, the amount of des-fluoro impurity in the isolated salt drops to approx. 40–60% of the original content in the raw (−)N-methyl paroxol. The yield of the isolated salt is up to 95%.

The purification power of the tosylate salt can be demonstrated in comparison with results of attempts to employ other salts in the purification process.

In converting a raw (−)N-methylparoxol to maleate, besylate or hydrochloride salt, the decrease of des-fluoro impurity was less than 10% (see Example 7 for details). On the contrary, the tosylate salt exhibited 51%.efficiency of the purification.

It is however not excluded that also other than tosylate salts may be experimentally proved to be suitable for purification purposes; such variant is within the spirit of our invention.

After converting the precipitated tosylate salt back to (−)N-methylparoxol by classical neutralisation, e.g. with an alkali metal hydroxide in aqueous environment, the amount of desfluoro-impurity may be still greater than 0.2%. Therefore, if the found amount of the desfluoro-impurity in the tosylate salt is still higher than 0.2%, the crystallisation step can be repeated prior to conversion. To do so, the salt is dissolved again in water at an elevated temperature, a small amount (0.1–0.2 molar) of p-toluene sulfonic acid added to the solution and the salt crystallised by cooling.

The same procedure can also be applicable for purification of the racemic trans-N-methyl-4-p-fluorophenyl-piperidine-3-carbinol (N-methylparoxol). However, the effect of the purification procedure under the above conditions is lower than in case of the above (−)trans isomer, only 15–20%. Nevertheless, the procedure still represents an effective purification method for decreasing the amount of des-fluoro impurity and may be applied in cases when the amount of des-fluoro impurity in the raw product only slightly exceeds the desired limit, as is the case with high yields and also allows the purification of N-methylparoxol from other related impurities.

Particularly, the procedure according to the present invention may be combined: After the racemic N-methylparoxol is purified via the tosylate salt, it is resolved into optical enantiomers, (e.g. by employing known resolution agents such as O,O-di-p-toluoyltartaric acid) and the resulting (−)N-methylparoxol is purified again via the tosylate salt.

The purified compounds of formula (1) resulting from the tosylate salts (8), especially the purified (−)N-methylparoxol, can be further converted into paroxetine of formula (2) by known procedures such as described in U.S. Pat. Nos. 4,007,196 and 4,721,723, which are generally characterised by, or involving, steps of converting compound (1) into a reactive derivative containing a leaving group such as halo or tosyloxy; a substitution reaction thereof with a donor of a 3,4-methylenedioxyphenyl moiety such as with sesamol or a salt thereof, and, optionally, followed by conversion of the R group, if different from hydrogen, to the hydrogen group.

This process may further comprise reacting the resulting paroxetine with a pharmaceutically acceptable acid to form a paroxetine acid addition salt. Preferred acids include hydrochloric acid, acetic acid, sulfonic acids (methane sulfonic acid etc.) and maleic acid, although other acids that form pharmaceutically acceptable acid addition salts may be used.

In relation with the intended use, the purified compounds (1) can be either used directly for production of paroxetine or may be first subjected to one or more steps of derivatisation on the nitrogen atom, resolution of optical isomers or conversion to salts, solvates or hydrates, by employing methods and conditions known per se.

Advantageously, the salt (8) itself can be used as a starting material for producing paroxetine instead of converting it back to the compound (1).

EXAMPLES

The following examples illustrate the invention but it should be understood that the present invention is by no means restricted to these specific examples. The analyses of des-fluoro impurity (7) were performed by HPLC with UV-detection at 210 nm, using a standard substance of (7), and the results are expressed in mass %.

Preparation of Starting Materials

Preparation 1:

Raw trans(±)-1-methyl-4-(p-fluorophenyl)piperidine-3-carbinol (N-methylparoxol)

The title compound was prepared by reduction of ethyl trans (±)-1-methyl-2,6-dioxo-4-(p-fluorophenyl)piperidine-3-carboxylate by lithium aluminium hydride in toluene/tetrahydrofurane according to the procedure of EP 223 334. The product was isolated as a free base.

Recrystallization of the raw compound with 2.54% of the des-fluoro impurity from various solvents gave the following contents of des-fluoro impurity:

| acetone | 2.50% | yield 83% |
| ethanol | 2.38% | 30% |
| methyl t-butylketone | 2.34% | 72% |
| toluene | 2.29% | 84% |
| isopropanol | 2.04% | 40% |

Preparation 2:

A Salt of (−)trans -1-methyl-4-(p-fluorophenyl)piperidine-3-carbinol with (−)-O,O-di-p-toluoyltartaric acid ((−)N-methylparoxol.DTT)

The compound was prepared by contacting of the raw racemic N-methylparoxol prepared as in Preparation 1, with (−)-O,O-di-p-toluoyltartaric acid in acetone followed by crystallisation of the salt after adding water and cooling, according to the procedure as outlined in EP 223334.

The decrease of the des-fluoro impurity content, in comparison with the starting material, was essentially 0%.

Recrystallization of a product having 0.76% of des-fluoro impurity from various solvents gave the following results:

| methanol | 0.76% | 88% yield |
| acetone/water | 0.76% | 87% |
| ethyl acetate/5% water | 0.78% | 88% |
| isopropanol/5% water | 0.78% | 96% |

Preparation 3:

(−)trans-1-methyl-4-(p-fluorophenyl)piperidine-3-carbinol ((−)N-methylparoxol)

The compound was prepared from the salt of Preparation 2 by contacting it with water solution of sodium hydroxide. Crude product precipitated and was collected and recrystallized from ethyl acetate.

The decrease of the des-fluoro impurity content, in comparison with the starting material, was essentially 0%.

Recrystallization of the product with 1.37% of des-fluoro impurity from methyl isobutylketone/n-pentane gave a product with 1.06% des-fluoro impurity in 70% yield; recrystallization of the same from ethyl acetate gave 1.15% in 81% yield.

EXAMPLES

Example 1

(−)trans -1-methyl-4-(p-fluorophenyl)piperidine-3-carbinol Tosylate Monohydrate 54.9 g of raw (−)N-methylparoxol (Preparation 3) was added under stirring to a solution of 43.4 g of p-toluene sulfonic acid monohydrate in 117 ml of water under stirring and the mixture was heated to 60 C. After dissolution, the solution was cooled to 20 C. and stirred at the same temperature for 1 hour. The formed crystals were filtered off, washed with 20 ml of cold water and dried. Yield: 91.4 g (89.8%).

The compound was identified by NMR and IR spectra, characterised by m.p. and optical rotation, the water content was determined by K. Fischer titration method. Several next batches prepared by essentially the same method were analysed by HPLC on the content of des-fluoro impurity:

| Starting compound: | 1.65% | 1.12% | 0.50% |
| Tosylate salt: | 0.72% | 0.55% | 0.25% |
| Purification efficacy: | 56.2% | 51.02% | 51.4% |
| Yield: | 80.3% | 96% | 85% |

Example 2
Recrystallization of (−)trans -1-methyl-4-(p-fluorophenyl)piperidine-3-carbinol Tosylate 91.4 g of (−)trans-1-methyl-4-(p-fluorophenyl)piperidine-3-carbinol tosylate monohydrate and 2.1 g of p-toluene sulfonic acid monohydrate were dissolved in 142 ml of water under stirring at 70–80 C. The solution was cooled to 20 C. and the mixture was stirred at this temperature for 1 hour. The formed crystals were filtered off, washed with 15 ml of cold water and dried. Yield: 78.5 g (86%)

Analysis by HPLC on the content of des-fluoro impurity in two next batches A, B prepared essentially by the same method:

| Starting salt: | A = | 0.25% | B = | 0.72% |
| Produced salt: | A = | 0.13% | B = | 0.40% |
| Yield: | A = | 94% | B = | 96% |

The produced salts A, B were subjected to one and two more recrystallizations, respectively, with the following results of des-fluoro impurity contents:

| A: | 0.07% (yield 91%) |
| B: | 0.25% (yield 90%) --> 0.15% (yield 95%) |

Example 3
(−)trans -1-methyl-4-(p-fluorophenyl)piperidine-3-carbinol Tosylate Monohydrate 100 g of (−)N-methylparoxol.DTT (compound of Preparation 2) was dissolved in 450 ml of ethyl acetate at 40–45 C. and 28.8 g of p-toluene sulfonic acid monohydrate was added under stirring. After dissolution, the solution was cooled to −10 C. and stirred for 3 hours. The precipitated crystals were filtered off, washed with 375 ml of ethyl acetate and dried. The yield was 60.4 g (90.2%)

| Analysis: | |
| Starting compound: | 0.96% des-fluoro imp. |
| Product: | 0.48% des-fluoro imp. |
| Efficacy: | 50.1% |
| Yield: | 96.7% |

Example 4
Trans(+/−)-1-methyl-4-(p-fluorophenyl)piperidine-3-carbinol Tosylate Monohydrate The compound was prepared by a method in Example 1, using N-methylparoxol (Preparation 1) as the starting material.

| Analytical results: | |
| Raw compound | 2.54% des-fluoro imp. |
| Tosylate | 1.03% des-fluoro imp. |
| Efficacy: | 59.5% |

The produced tosylate compound was recrystallized from water essentially as described in Example 2 with the following results:

| Desfluoro-impurity content: | 0.73% |
| Yield: | 75.9% |

Example 5
(−)trans-1-methyl-4-(p-fluorophenyl)piperidine-3-carbinol (purified (−)N-methylparoxol)

100 g of toluene was mixed with a solution of 6 g of NaOH in 590 ml of water and 57.4 g of (−)trans-1-methyl-4-(p-fluorophenyl)piperidine-3-carbinol tosylate monohydrate was added to the mixture under stirring. The emulsion was stirred for 15 minutes and then allowed to stand for separation of layers. Toluene layer was washed with 80 ml of water and separated. 70 g of n-hexane was added to the toluene solution and the mixture was cooled to 0–5 C. under stirring. At this temperature, the mixture was stirred for next 5 hours. Precipitated solid was filtered off, washed with 20 g of n-hexane and dried. Yield 26.8 g (85,6%)

The analytical results were following:

| Des-fluoro in starting tosylate: | 0.07% |
| Des-fluoro in the carbinol: | 0.065% |

Example 6
Paroxetine from (−)N-methylparoxol

Paroxetine hydrochloride was prepared from (−)N-methylparoxol by the following synthetic scheme (−)N-methylparoxol->N-methylparoxetine->Paroxetine according to known synthetic procedure as basically outlined in U.S. Pat. No. 3,912,473 and U.S. Pat. No. 4,007,196. Paroxetine was isolated as a hydrochloride. As starting materials, raw and purified (−)N-methylparoxol (cf. Preparation 3 and/or Example 5) were used. The content of corresponding des-fluoro impurities in both reaction series was monitored by HPLC at the following stages.

| % of des-fluoro in | raw | purified |
| --- | --- | --- |
| (−)N-methylparoxol | 0.64 | 0.18 |
| N-methylparoxetine | 0.53 | 0.14 |
| Paroxetine.HCl | 0.34 | 0.08 |

Example 7
Comparison of Efficacy of Purification (−)N-methylparoxol with the des-fluoro impurity content of 1.12% was converted to the tosylate salt as described in Example 1. The same batch of (−)N-methylparoxol was converted into salts with other acids by methods known per se and the salts were isolated by crystallisation.

|  | Des-fluoro | purification efficiency |
| --- | --- | --- |
| maleate | 1.15% | −4.1% |
| besylate | 1.09% | 2.0% |
| hydrochloride | 1.07% | 4.8% |
| tosylate | 0.55% | 51%. |

The invention having been described, it will be readily apparent to those skilled in the art that further changes and modifications in actual implementation of the concepts described herein can easily be made or may be learned by practice of the invention, without departing from the spirit and scope of the invention as defined by the following claims.

What is claimed is:

1. A compound of formula (8):

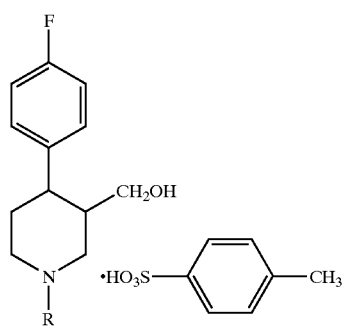

(8)

wherein R represents hydrogen, a lower alkyl group, an aryl group, an alkoxycarbonyl group or an aryloxycarbonyl group.

2. The compound according to claim 1, wherein said compound is in a crystalline state.

3. The compound according to claim 2, wherein said crystalline compound has a content of about 0.2% or less of a desfluoro impurity of formula (7):

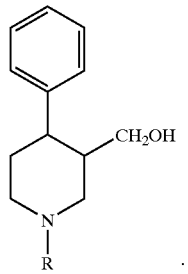

(7)

4. The compound according to claim 1, wherein the substituents in the position 3 and 4 are in trans- orientation with respect to each other.

5. The compound according to the claim 4, wherein said compound is the (3S, 4R) trans optical isomer.

6. The compound according to claim 1, wherein R represents a methyl group.

7. The compound according to claim 6, wherein said compound is (−) trans-4- (p-fluorophenyl)-1-methyl-3-piperidinecarbinol p-toluene sulfonate.

8. The compound according to claim 7, wherein said compound is (−) trans-4- (p-fluorophenyl)-1-methyl-3-piperidinecarbinol p-toluene sulfonate monohydrate.

9. A process which comprises contacting a compound of formula (1)

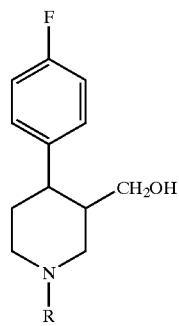

(1)

or a salt thereof which contains a des-fluoro impurity of formula (7)

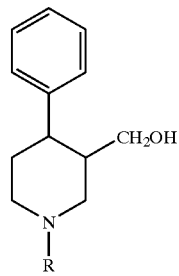

(7)

wherein R in both compounds (1) and (7) represents a hydrogen atom, a lower alkyl group, an aryl group, an alkoxycarbonyl group or an aryloxycarbonyl group, with toluene sulfonic acid in a solvent to form a salt of formula (8):

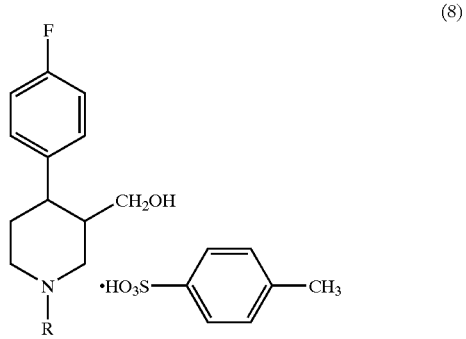

(8)

wherein R has the same meaning as in formula (1).

10. The process according to claim 9, wherein said solvent is selected from water, ethyl acetate and a 1:1 mixture of methanol and ethyl acetate.

11. The process according to claim 9, which further comprises separating the compound of formula (8) in a solid state from said solvent.

12. The process according to claim 11, wherein said compound of formula (8) is separated by crystallization from said solvent.

13. The process according to claim 12, wherein said crystalline compound of formula (8) contains 40 to 60% of the initial amount of des-fluoro impurity of formula (7).

14. The process according to claim 13, which further comprises recrystallizing said compound of formula (8).

15. The process according to claim 14, wherein additional toluene sulfonic acid is added to the recrystallization solvent.

16. The process according to claim 9, wherein said compound of formula (1) is N-methylparoxol.

17. The process according to claim 16, wherein said compound of formula (8) contains 0.1% or less of the impurity of formula (7).

18. The process according to claim 16, wherein said compound of formula (1) is the di-p-toluoyltartrate salt of N-methylparoxol.

19. The process according to claim 16, which further comprises neutralizing said compound of formula (8) to re-form said compound of formula (1) with less than 0.1% of the des-fluoro impurity of formula (7).

20. The process according to claim 19, which further comprises converting said purified compound of formula (1) into paroxetine.

21. The compound according to claim 1, wherein R represents a lower alkyl.

22. The process according to claim 9, wherein R represents a lower alkyl.

23. The process according to claim 22, wherein R represents methyl.

24. The process according to claim 10, wherein R represents a lower alkyl.

25. The process according to claim 13, wherein R represents a lower alkyl.

* * * * *